United States Patent
Sweitzer et al.

(10) Patent No.: US 11,684,487 B2
(45) Date of Patent: Jun. 27, 2023

(54) SURGICAL HAMMER

(71) Applicant: Shukla Medical, St. Petersburg, FL (US)

(72) Inventors: Zachary Robert Sweitzer, Keyport, NJ (US); Nicholas Christopher Keach, Lutz, FL (US)

(73) Assignee: Shukla Medical, St. Petersburg, FL (US)

( * ) Notice: Subject to any disclaimer, the term of this patent is extended or adjusted under 35 U.S.C. 154(b) by 19 days.

(21) Appl. No.: 16/787,500

(22) Filed: Feb. 11, 2020

(65) Prior Publication Data

US 2021/0093464 A1     Apr. 1, 2021

Related U.S. Application Data

(60) Provisional application No. 62/908,813, filed on Oct. 1, 2019.

(51) Int. Cl.
*A61F 2/46* (2006.01)

(52) U.S. Cl.
CPC ........ *A61F 2/46* (2013.01); *A61F 2002/4619* (2013.01); *A61F 2002/4681* (2013.01)

(58) Field of Classification Search
CPC ............... A61F 2/46; A61F 2002/4619; A61F 2002/4681; A61B 17/92; A61B 2017/922; B25D 1/12; B25D 1/02; B25D 1/00; B25D 1/04; B25D 1/045; B25D 1/14
USPC ...... 81/22, 20; 254/18, 25; 173/90, 126, 131
See application file for complete search history.

(56) References Cited

U.S. PATENT DOCUMENTS

| | | | | |
|---|---|---|---|---|
| 2,989,101 | A * | 6/1961 | Carmien | B25D 1/12 81/19 |
| 6,435,059 | B1 * | 8/2002 | Martinez | B25D 1/06 81/20 |
| 9,016,171 | B2 * | 4/2015 | Chen | B25D 1/12 81/22 |
| 9,044,846 | B1 * | 6/2015 | Dawson | B25D 1/12 |
| 9,839,448 | B2 * | 12/2017 | Reckling | A61B 17/17 |
| 2007/0113709 | A1 * | 5/2007 | Krallman | B25D 1/045 81/22 |
| 2014/0371754 | A1 | 12/2014 | Buttler et al. | |
| 2018/0028224 | A1 | 2/2018 | Lee et al. | |
| 2018/0116821 | A1 | 5/2018 | Johannaber et al. | |
| 2019/0290449 | A1 | 9/2019 | Wu et al. | |

OTHER PUBLICATIONS

International Search Report and the Written Opinion of the International Searching Authority, PCT/US2020/042059, dated Nov. 6, 2020.
Indian Examination Report dated Jun. 17, 2022 in Indian Application No. 202247024903.

* cited by examiner

*Primary Examiner* — Kevin T Truong
*Assistant Examiner* — Tracy L Kamikawa
(74) *Attorney, Agent, or Firm* — Kim IP Law Group LLC (57) ABSTRACT

A surgical hammer that includes a handle, a shaft extending from the handle and a hammer head connected to the shaft. The hammer head includes a slot extending through the hammer head and in fluid communication with a distal end of the hammer head, a first internal cavity within the hammer head spaced laterally from the slot, and a second internal cavity within the hammer head spaced laterally from the slot.

20 Claims, 7 Drawing Sheets

SURGICAL HAMMER

BACKGROUND OF THE DISCLOSURE

Exemplary embodiments of the subject disclosure relate generally to the field of medical device implant extraction tools. Specifically, the subject disclosure relates to a surgical hammer.

Oftentimes when performing an implant revision surgery, and when performing any type of surgery, it becomes necessary or desirable to direct a force accurately along a shaft or shank of a surgical device to apply a force parallel to the shaft or shank. The subject disclosure provides an improved surgical hammer to address this need.

SUMMARY OF THE DISCLOSURE

One exemplary embodiment of the subject disclosure provides a surgical hammer that includes a handle, a shaft extending from the handle and a hammer head connected to the shaft. The hammer head includes a slot extending through the hammer head and in fluid communication with a distal end of the hammer head, a first internal cavity within the hammer head spaced laterally from the slot, and a second internal cavity within the hammer head spaced laterally from the slot. In certain embodiments, the slot is between the first internal cavity and the second internal cavity.

In certain exemplary embodiments, at least a portion of each of the first internal cavity and the second internal cavity is filled with a solid material (e.g., a metal), such as metal ball bearings or shot. The first internal cavity and the second internal cavity can be partially or completely filled. For example, the metal bearings or shot can occupy, by volume, from about 20% to about 95% of the internal volume of each of the first internal cavity and the second internal cavity. In exemplary embodiments, each of the first internal cavity and the second internal cavity is a cylindrical cavity.

In certain exemplary embodiments, the first internal cavity and the second internal cavity have an overall volume of about 40% to 70% of an overall volume of the hammer head. In certain embodiments, the shaft is connected to the hammer head about its proximal end and/or about its longitudinal midportion. In exemplary embodiments, the slot is an elongated slot having a longitudinal axis parallel to a longitudinal axis of the shaft. In certain embodiments, the slot is a tapered slot. In certain embodiments, the hammer includes a convex surface defining a proximal end of the slot.

In certain exemplary embodiments, the hammer head has a substantially cylindrical overall profile. For example, the hammer head can have an overall weight of about 100 grams to 5 kilograms.

Another exemplary embodiment of the subject disclosure provides a surgical hammer that includes a handle, a shaft extending from the handle and a substantially cylindrical hammer head connected to the shaft about its proximal end and its longitudinal midportion. The hammer head includes an elongated tapered slot extending through the hammer head and in fluid communication with a distal end of the hammer head, a cylindrical first internal cavity within the hammer head spaced laterally from the elongated tapered slot and at least partially filled with metal ball bearings or shot, and a cylindrical second internal cavity within the hammer head spaced laterally from the elongated tapered slot and at least partially filled with metal ball bearings or shot.

BRIEF DESCRIPTION OF THE SEVERAL VIEWS OF THE DRAWINGS

The following detailed description of an exemplary embodiment of the subject disclosure will be better understood when read in conjunction with the appended drawings. For the purpose of illustrating the present disclosure, there is shown in the drawings an exemplary embodiment. It should be understood, however, that the subject application is not limited to the precise arrangements and instrumentalities shown.

DETAILED DESCRIPTION

Reference will now be made in detail to an exemplary embodiment of the subject disclosure illustrated in the accompanying drawings. Wherever possible, the same or like reference numbers will be used throughout the drawings to refer to the same or like features. It should be noted that the drawings are in simplified form and are not drawn to precise scale. In reference to the disclosure herein, for purposes of convenience and clarity only, directional terms such as upper, lower, top, bottom, above, below and diagonal, are used with respect to the accompanying drawings. Such directional terms used in conjunction with the following description of the drawings should not be construed to limit the scope of the subject disclosure in any manner not explicitly set forth. Additionally, the term "a," as used in the specification, means "at least one." The terminology includes the words above specifically mentioned, derivatives thereof, and words of similar import.

"About" as used herein when referring to a measurable value such as an amount, a temporal duration, and the like, is meant to encompass variations of ±20%, ±10%, ±5%, ±1%, or ±0.1% from the specified value, as such variations are appropriate.

"Substantially" as used herein shall mean considerable in extent, largely but not wholly that which is specified, or an appropriate variation therefrom as is acceptable within the field of art.

Throughout the subject application, various aspects thereof can be presented in a range format. It should be understood that the description in range format is merely for convenience and brevity and should not be construed as an inflexible limitation on the scope of the subject disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Furthermore, the described features, advantages and characteristics of the exemplary embodiments of the subject disclosure may be combined in any suitable manner in one or more embodiments. One skilled in the relevant art will recognize, in light of the description herein, that the subject disclosure can be practiced without one or more of the specific features or advantages of a particular exemplary embodiment. In other instances, additional features and advantages may be recognized in certain embodiments that may not be present in all exemplary embodiments of the present disclosure.

Referring now to the drawings, FIG. 1-7 illustrate a surgical hammer (100) according to an exemplary embodiment of the present disclosure. The surgical hammer includes a handle (102) and a shaft (104) extending from the handle. A hammer head (106) is connected to the shaft (104) and includes a slot (108). The slot (108) extends through the hammer head (106) and is in fluid communication with a distal end (110) of the hammer head.

As shown best in FIG. 6A and as will be discussed in greater detail below, the hammer head (106) in this exemplary embodiment includes a first internal cavity (612) spaced laterally from the slot (108) and a second internal cavity (614) that is also spaced laterally from the slot (108). In alternative embodiments, the hammer head (106) can have one or more internal cavities located within the hammer head at any location.

The handle (102) can include a scaffold (605) that runs the longitudinal length of the handle. The scaffold includes a radial flare (607) about a proximal end (101) of the handle (102) and the surgical hammer (100), and a second radial flare (609) about a distal end (103) of the handle. In this particular embodiment, the radial flare (607) and second radial flare (609) have the same diameter. Along the length between the radial flare (607) and the second radial flare (609) the scaffold (605) in this embodiment is generally circular in cross-sectional shape and has a reduced diameter, where a series of apertures (611) can optionally be provided to, for example, facilitate engagement with the gripper (613) during molding, or a like process.

The gripper (613) is secured about the scaffold (605) and forms the outer surface of the handle (102). The gripper and can be composed of a variety of materials that facilitate efficient and/or ergonomic manual manipulation of the surgical hammer (100). In this exemplary embodiment, the gripper has a relatively larger diameter about a midportion (115) of the handle (102) having a diameter approximately the same, or the same as the diameter of the radial flares (607, 609). The gripper (613) tapers from the midportion (115) to a reduced diameter as shown in FIGS. 1-7, and then tapers outward to circumscribe the radial flare (607) about the proximal end (101) of the handle (102) and the second radial flare (609) about the distal end (103) of the handle (102). Other designs can be provided, as the above description is provided for purposes of illustration and not limitation.

The second radial flare (609) can contain a centrally located threaded bore (617) about the distal end (103) of the handle shaped to receive a complimentary threaded, proximal portion (619) of the shaft (104). As shown in FIG. 6A, the proximal portion (619) of the shaft that engages with the scaffold (605) has a reduced diameter as compared to the rest of the shaft (104). In this embodiment, the shaft (104), including its proximal portion (619), have a circular or generally circular cross-sectional shape, though the shaft (104) can alternatively have different shapes.

The shaft (104) extends distally to a threaded portion (621) about a distal end (627) of the shaft (104). The threaded portion (621) has a circular cross-sectional shape. A bore (623) is provided in a body (641) of the hammer head about a proximal end (116) of the hammer head (106) that is sized to receive, and is provided with threads complimentary to, the threaded portion (621). The center of the bore (623) is located along the longitudinal midportion (524) of a longitudinal length (I) of the hammer head (106). As shown best in FIGS. 6A and 6B, the distal end of the shaft (627) approaches the proximal end (125) of the slot (108) as assembled (e.g., the distal end (627) is within 5, 4, 3, 2 or 1 mm of the proximal end (125) of the slot (108)).

As shown in the FIGS., the hammer head (106) in this exemplary embodiment has a cylindrical overall shape, more particularly a right circular cylindrical overall shape. The slot (108) extends through the body (641) of the hammer head about the longitudinal midportion (524) of the hammer head (106), dissecting the cylinder and creating a first cylindrical portion (130) about one side of the hammer head (106) and a second cylindrical portion (132) about an opposite side of the hammer head (106).

Figure 1:
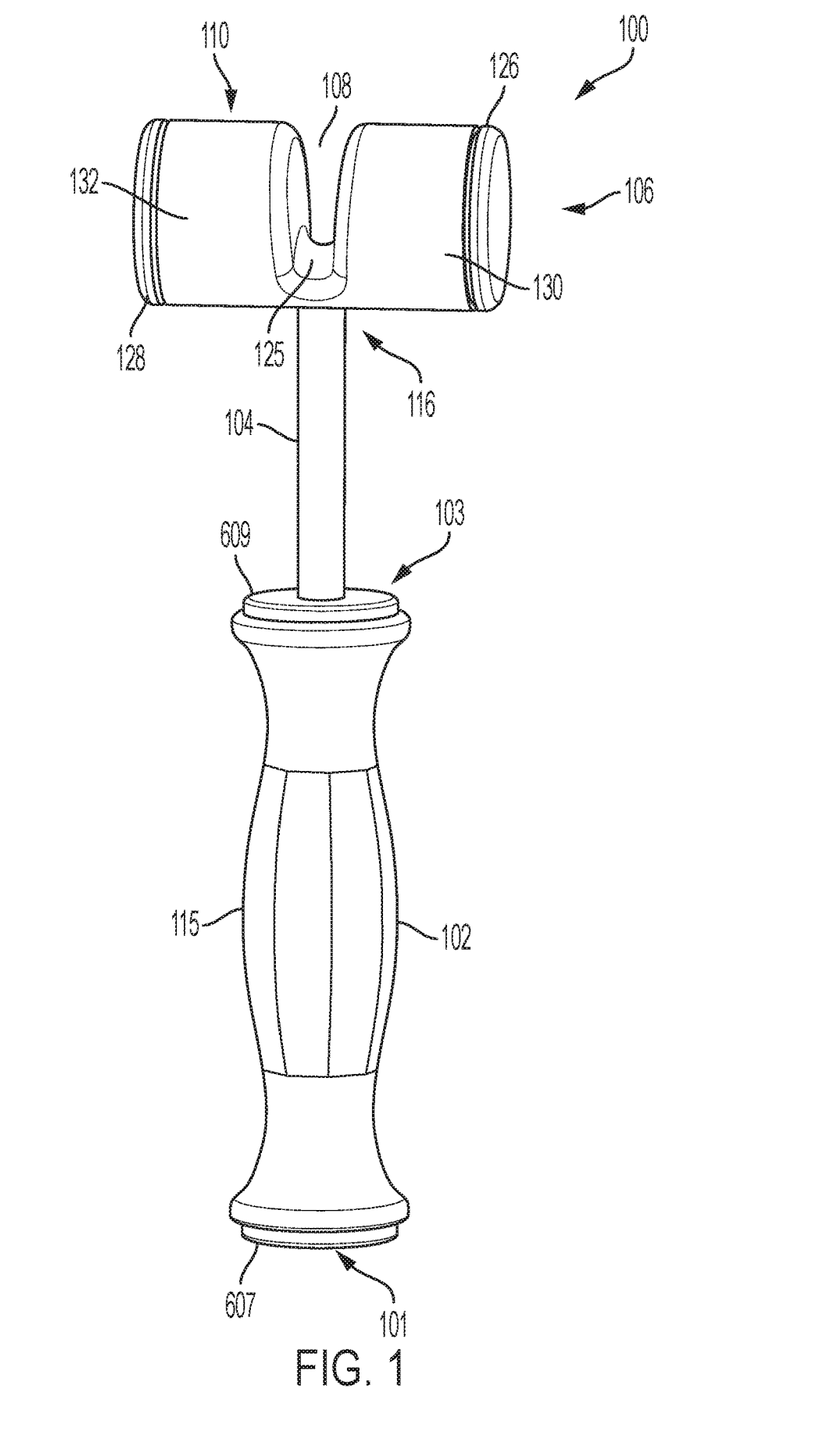
FIG. 1 is a perspective view of a surgical hammer in accordance with an exemplary embodiment of the subject disclosure.
Figure 2:
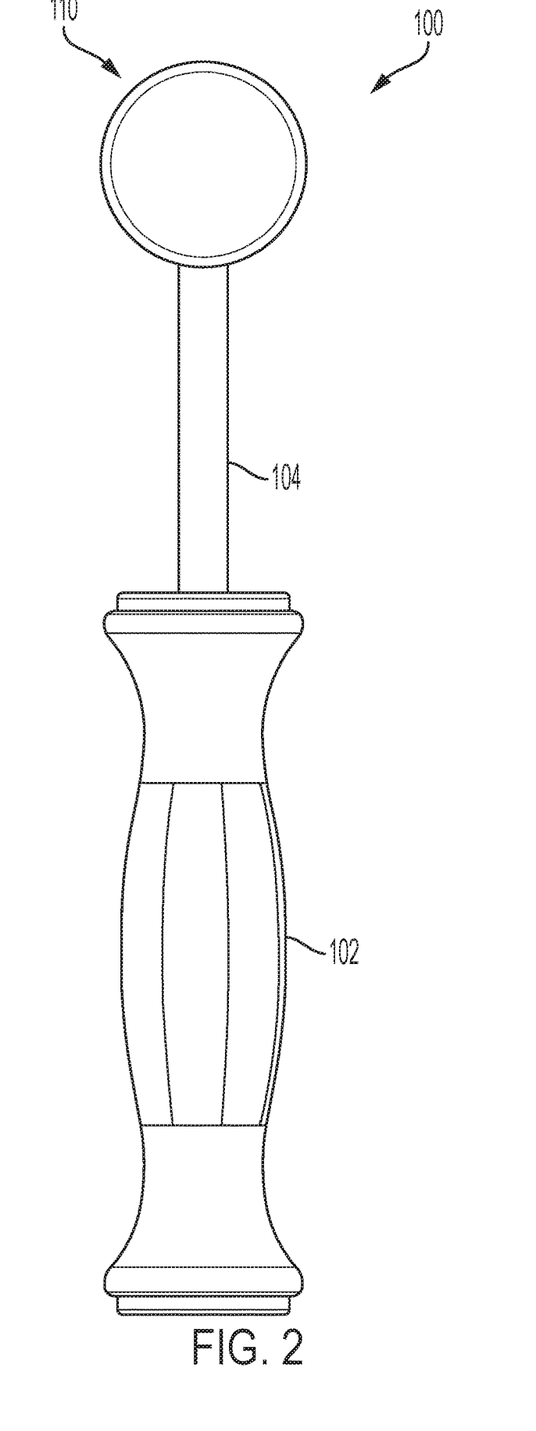
FIG. 2 is a left side view of the surgical hammer of FIG. 1.
Figure 3:
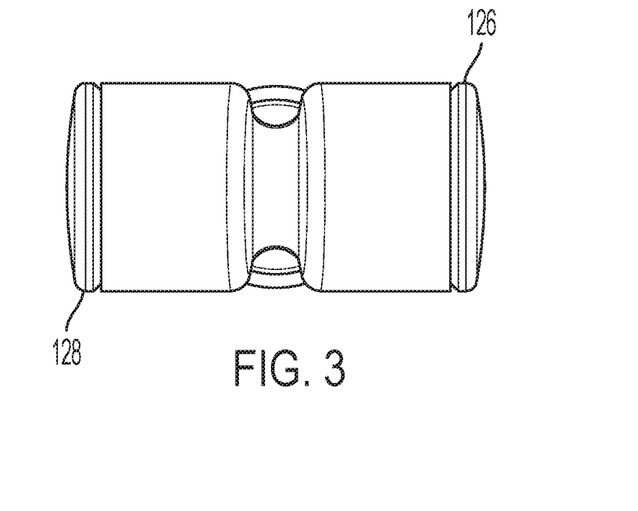
FIG. 3 is a top plan view of the surgical hammer of FIG. 1.
Figure 4:
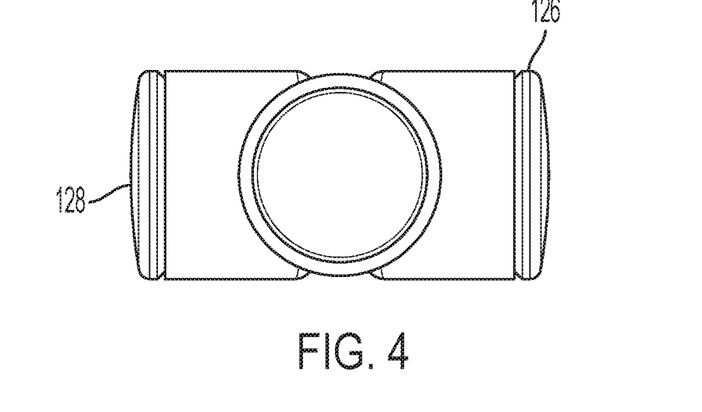
FIG. 4 is a bottom plan view of the surgical hammer of FIG. 1.
Figure 5:
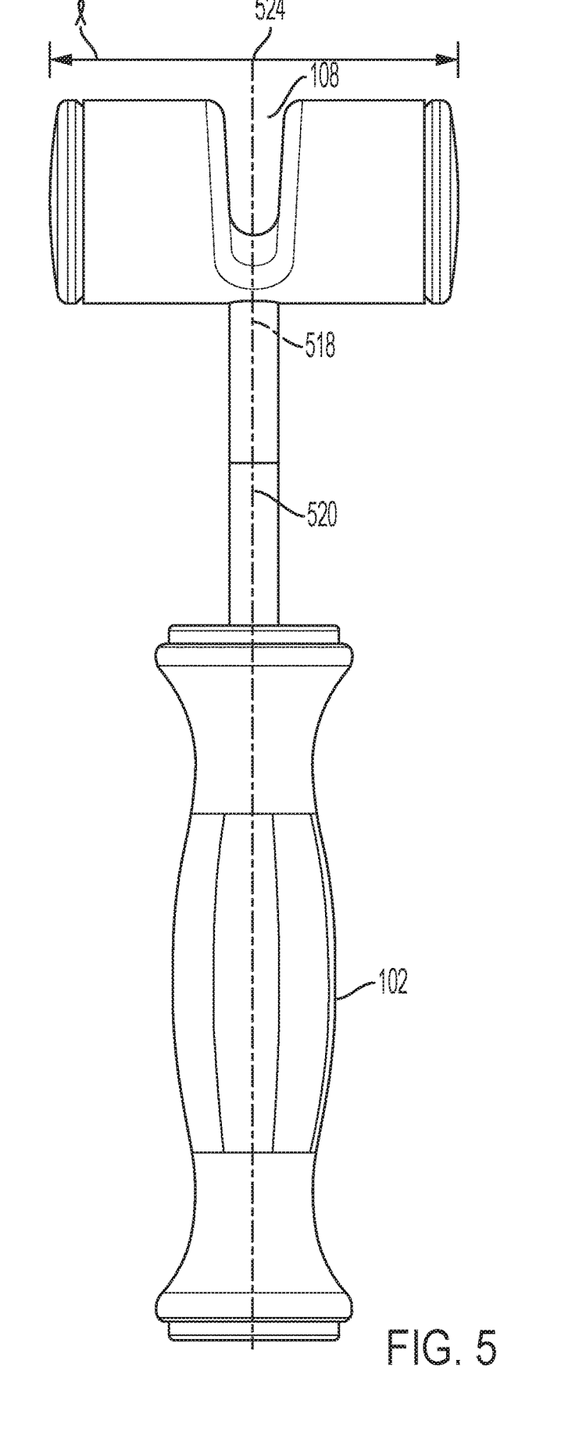
FIG. 5 is a front view of the surgical hammer of FIG. 1.

As shown best in FIG. 5, the slot (108) is an elongated slot having a longitudinal axis (518) that is coaxial with, and/or parallel to, the longitudinal axis (520) of the shaft (104). The slot (108) is also a tapered slot, in which the width of the slot at the distal end (110) of the hammer is the widest, with the width gradually tapering to smaller widths as the slot approaches the proximal end (125) of the slot.

Figure 6A:
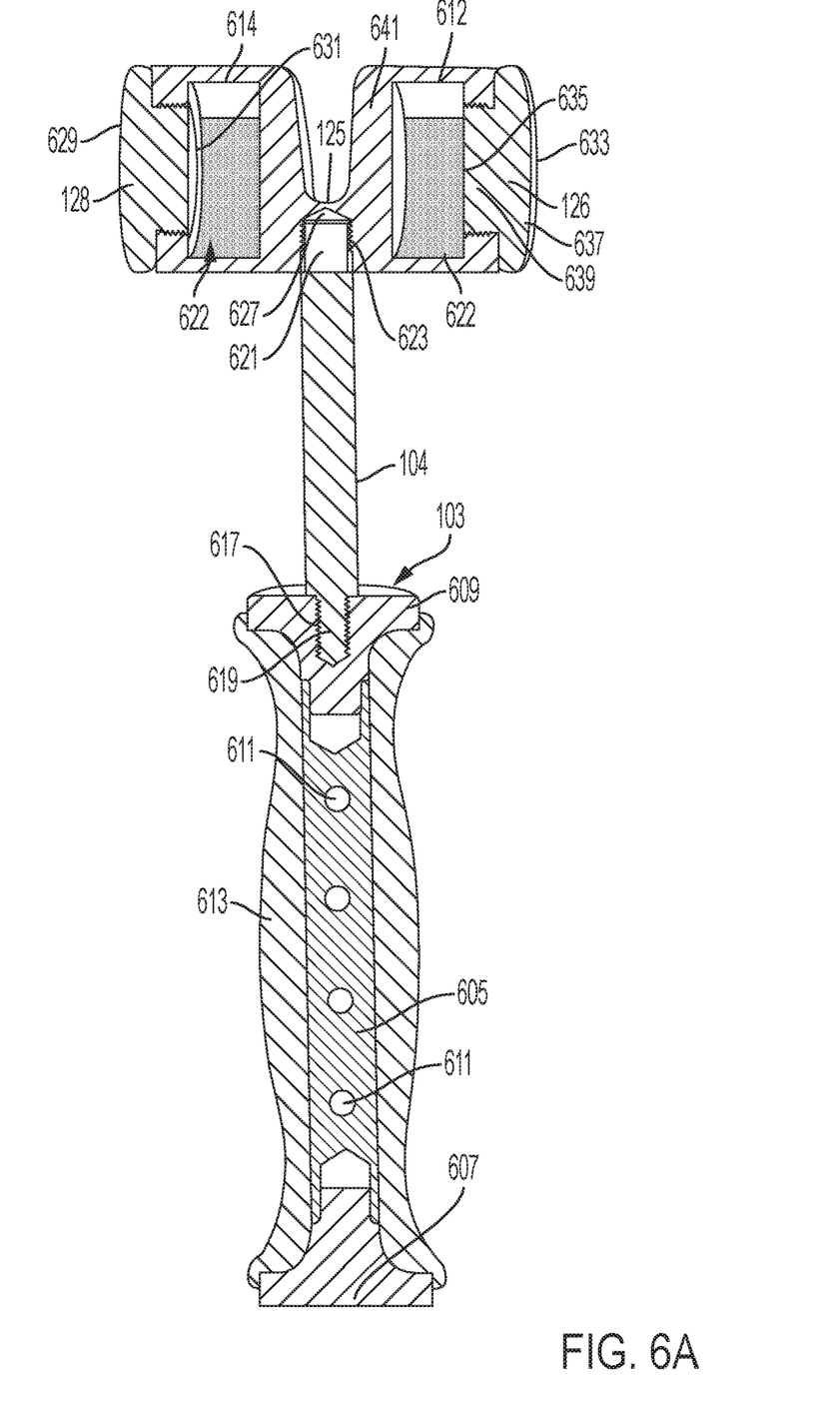
FIG. 6A is a cross-sectional view of the surgical hammer of FIG. 1.
Figure 6B:
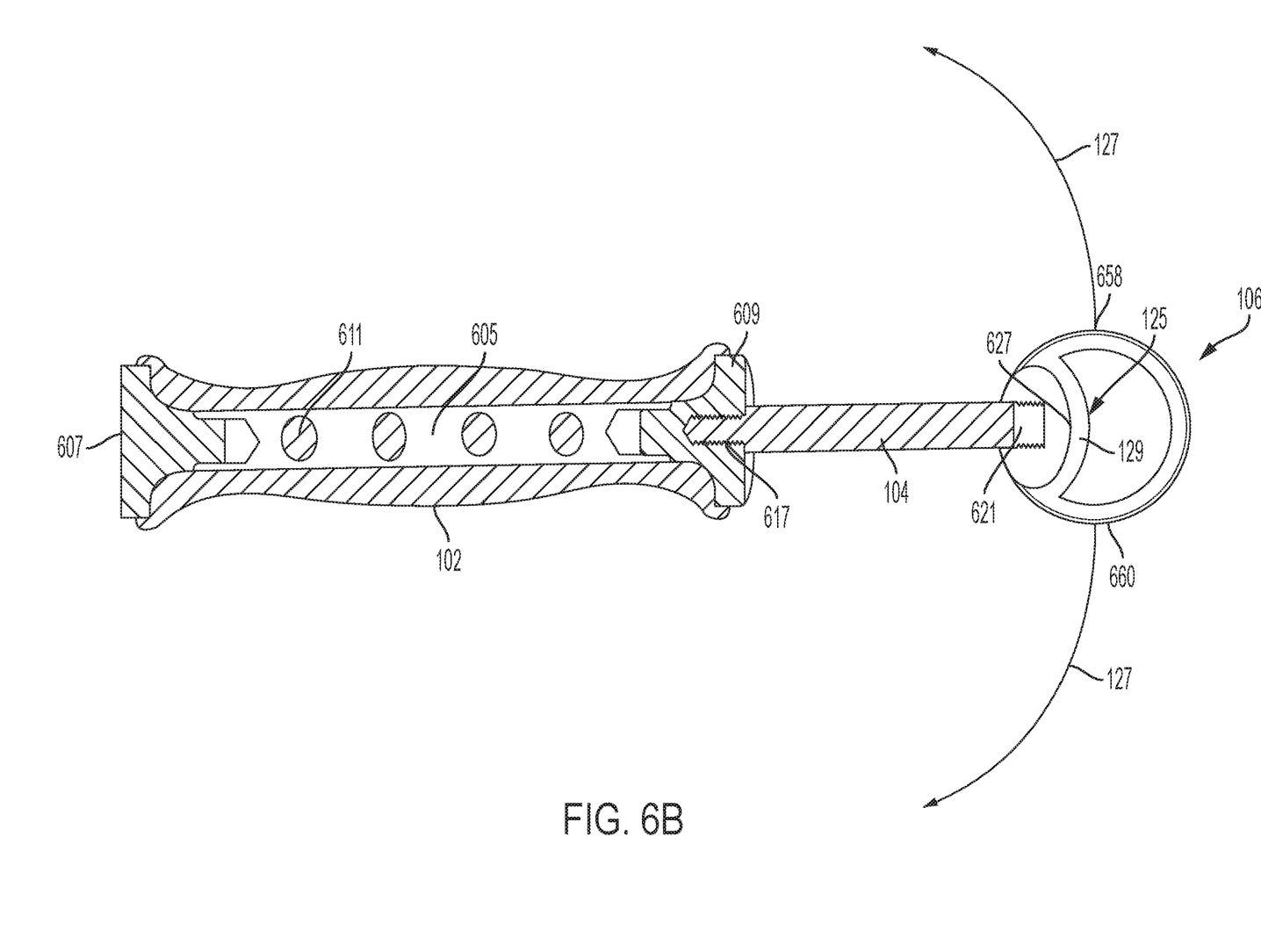
FIG. 6B is another cross-sectional view of the surgical hammer of FIG. 1.

FIG. 6B is a cross-sectional view along the longitudinal midportion (524) of the shaft (104). As shown there, the proximal end (125) of the slot of the hammer includes a convex surface (129) that defines a proximal end of the slot. The convex surface curves symmetrically, inwardly as it approaches oppositely-faced striking surfaces (658,660) of the body (641) of the hammer head (106). The convex surface (129) is between the first and second internal cavities.

As explained in greater detail below, in operation the surgical hammer is positioned such that a shaft or shank of an object to be struck is situated within the slot. In the exemplary embodiment shown in FIG. 6B, the convex shape of the proximal end (125) substantially matches a swing plane (127) of the hammer head (104) when swung by a user with a natural wrist motion, in which the user will naturally hinge or cock their wrist on the upswing, which will tend to bring the hammer head away from a longitudinal plane of the shaft of the object to be struck, and then unhinge or release their wrist on the downswing, which will again tend to bring the hammer head away from the plane of the longitudinal plane of the shaft. The convex shape (129) at the proximal end (125) of the slot (106) in this particular embodiment accounts for this natural swing plane (127) of the hammer head and allows for the proximal end (125) of the slot (108) to maintain better contact with the shaft or other straight guide as the hammer head is swung by a user throughout an entire range of motion to efficiently deliver force to the struck object (e.g., to a strike plate of the struck object).

The body (641) of the hammer head through which the slot (108) is formed contains a first internal cavity (612) along one side of the slot (108) and a second internal cavity (614) along the other side of the slot (108). As shown best in FIG. 6A, a portion the first and second internal cavities are cylindrical and a portion of the first internal cavity (612) and a portion of the second internal cavity (614) are filled with a solid material, such as a metal or other dense substance. A partial portion as shown in FIG. 6A, or an entire portion of the first internal cavity and/or the second internal cavity can be filled with the solid material. In this particular embodiment the first and second internal cavities are filled with metal bearings or shot (622).

For example, in certain embodiments, the first internal cavity (612) and the second internal cavity (614) have an overall volume of from 25% to about 85% (e.g., from 40% to about 70%) of an overall volume of the hammer head (106). The first and second internal cavities can alternatively be larger or smaller to provide larger or smaller volumes. The first and second cavities can have the same size and volume, or they can have different sizes and volumes than the other. In this particular embodiment, the first and second cavities have substantially the same size and volume.

In exemplary embodiments, the first internal cavity (612) and the second internal cavity (614) are filled completely with the solid material such that the individual components (e.g., individual ball bearings or shot (622)) do not have room to move within the cavity upon use.

Alternatively, in exemplary embodiments, the first internal cavity (612) and/or the second internal cavity (614) are partially filled as shown in FIG. 6A. A partially filled cavity can be provided to suppress a ringing sound or reverberation of the hammer head that can occur during striking. In exemplary embodiments, the first cavity (612) and/or the second internal cavity (614) are partially filled to an extent such that the hammer head cavity acoustically resembles a tuning fork, in which the shot or individual ball bearings dampens the vibrations that cause sound. In addition, or in the alternative, the first internal cavity (612) and/or the second internal cavity (614) are partially filled to an extent such that the hammer head provides a dead-blow effect, in which a bounce-back or rebound of the hammer head from the struck object is reduced upon impact.

In one embodiment, solid material (e.g., shot (622)) occupies, by volume, from about 5% to about 98%, or from about 20% to about 95%, or from about 50% to about 90% of the total internal volume of the first internal cavity (612) and/or the second internal cavity (614), including, e.g., 10%, 15%, 20%, 25%, 30%, 35%, 40%, 45%, 50%, 55%, 60%, 65%, 70%, 75%, 80%, 85%, 90% and 95%.

The volumes of the first internal cavity (612) and the second internal cavity (614), and/or the extent to which (e.g., by volume) the first internal cavity (612) and the second internal cavity (614) is filled with solid material, can be varied based on the desired weight of the hammer head (104), and to yield a desired force upon impact by the hammer.

In an exemplary embodiment, the hammer head has an overall weight of from about 100 g to 5 kg. For example, the hammer head can have an overall weight of from about 500 g to 4 kg or from about 1 kg to 3 kg. Other weights can be provided based on the application. For example, for more delicate surgical procedures the hammer head can have an overall weight of less than 100 g, or less than 50 g (e.g., as low as about 10 g). Alternatively, for more invasive procedures, such as orthopedic procedures involving large limbs, the hammer head can have an overall weight higher than 1 kg, or higher than 3 kg, or higher than 5 kg (e.g., up to about 10 kg). Other hammer head weights can be provided, including e.g., 200 g, 300 g, 400 g, 500 g, 600 g, 700 g, 800 g, 900 g, 2 kg, 4 kg, 6 kg, 7 kg, 8 kg, and 9 kg.

The surface of the body (641) around the first cylindrical portion (130) and the second cylindrical portion (132) forms the striking surfaces (658, 660) for contacting medical devices (e.g., medical implants and tools associated with extracting medical implants). Thus the body (641), and the hammer head (106) generally, can be composed of a suitably hard, material such as a metal, a ceramic, or a composite such as, but not limited to, stainless steel, aluminum, copper, tin or a mild steel. Other configurations can be provided in accordance with the subject disclosure.

A first cap (126) is provided about an end of the first cylindrical portion (130), which forms an end of the hammer head (106) itself along one end (633) (e.g., a lateral end) of the first cap (126) and also forms a boundary to the first internal cavity (612) along an opposite end (635) of the first cap. A second cap (128) is provided about an end of the second cylindrical portion (132) and forms an opposite end (629) of the hammer head (106) and also a boundary to the second internal cavity (614) along an opposite end (631) of the second cap (128). In certain embodiments, the first cap (126) and the second cap (128) can provide second striking surfaces about the lateral ends (629, 633).

As shown in FIG. 6A, the first cap (126) has a first circular section (637) about the end (633) that has the same, or substantially the same diameter as the overall diameter of the cylindrical hammer head (106) itself, and a second circular section (639) that is threaded and has a relatively smaller diameter. In this exemplary embodiment, the ends of the body (641) contain bores sized to receive the second circular section (639) of the first cap (126), the bore being provided with threads complementary to the threads in the second circular section (639) of the first cap (126). The second cap (128) is engaged with the body (641) in the same manner. Alternatively, for example, a non-threaded bore can be provided and the section circular section (639) of the first cap (126) and the end of the body can be sized to provide, for example, a press-fit or slip-fit engagement. Furthermore, for example, welding and/or an epoxy can optionally be employed to further secure the first and second caps (126, 128) to the end of the body (641).

The first internal cavity (106) and the second internal cavity (108) can be filled with the shot (622) and the first cap and the second cap can be engaged (e.g., screwed into) the body (641) to secure the shot (622) within the cavities. The outer circumference of the ends (629, 633) of the first and second caps can be optionally permanently secured (e.g., by welding) or otherwise sealed and provided with a finish.

In operation, for example, a user of the instantly disclosed surgical hammer can insert the slot (104) around the shaft or shank of a surgical device, and apply a force to that surgical device while using the shaft or shank of the medical device as a guide to efficiently direct movement of the hammer head parallel to the shaft or shank.

Figure 7A:
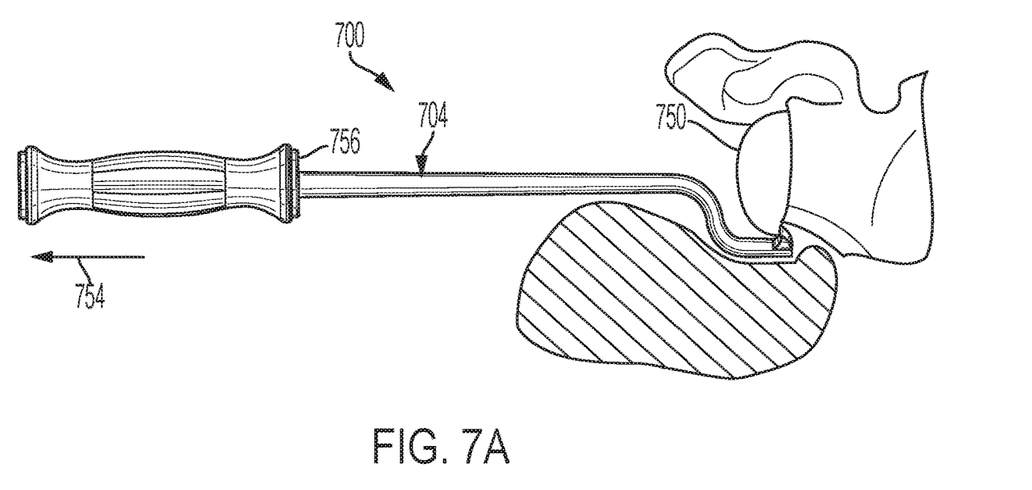
FIG. 7A is an exemplary surgical device that can be used in conjunction with the surgical hammer of FIG. 1.
Figure 7B:
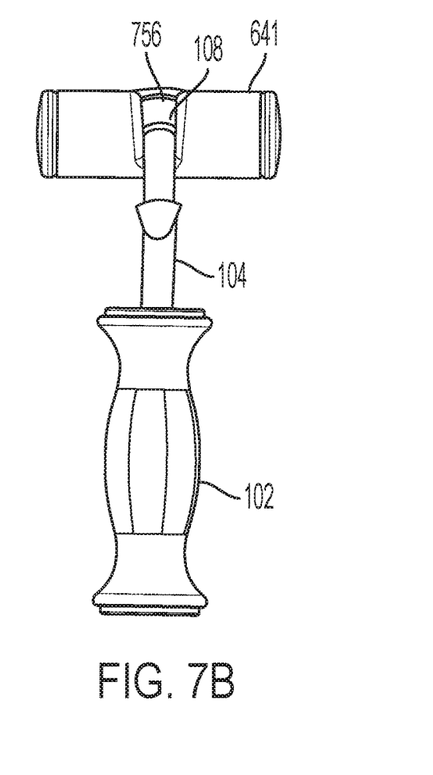
FIG. 7B depicts the surgical hammer of FIG. 1 engaged with the surgical device of FIG. 7A.

FIG. 7A depicts an exemplary medical device (700) to which the instantly disclosed surgical hammer (100) can be applied. For example, a user could insert the slot (108) of the instantly disclosed surgical hammer into and around shank (704) of the medical device (700) as shown in FIG. 7B. One would then swing or drop the hammer head in direction (754) to contact strike plate (756) of the medical device (700) with the body of the hammer head. Doing so will assist in the removal of the medical implant (750).

It will be appreciated by those skilled in the art that changes could be made to the exemplary embodiments described above without departing from the broad inventive concept thereof. It is to be understood, therefore, that this disclosure is not limited to the particular embodiments disclosed, but it is intended to cover modifications within the spirit and scope of the claims defined herein.

The invention claimed is:

1. A surgical hammer comprising:
   a handle;
   a shaft extending from the handle; and
   a hammer head connected to the shaft, the hammer head including:
      a slot extending through the hammer head and in fluid communication with a distal end of the hammer head, wherein the slot is gradually tapered from the distal end of the hammer head to a proximal end of the slot,
      a bore extending into the hammer head sized to receive the shaft,
      a first internal cavity within the hammer head spaced laterally from the slot, and
      a second internal cavity within the hammer head spaced laterally from the slot, wherein the slot is distal to the bore at a longitudinal midportion of the hammer head, between the first internal cavity and the second internal cavity.

2. The surgical hammer of claim 1, wherein a portion of each of the first internal cavity and the second internal cavity is filled with a metal.

3. The surgical hammer of claim 2, wherein the first internal cavity and the second internal cavity are partially filled.

4. The surgical hammer of claim 2, wherein each of the first internal cavity and the second internal cavity is filled with metal from about 20% to 95% by volume.

5. The surgical hammer of claim 2, wherein each of the first internal cavity and the second internal cavity is filled to capacity with metal.

6. The surgical hammer of claim 1, wherein a portion of each of the first internal cavity and the second internal cavity is filled with metal ball bearings or shot.

7. The surgical hammer of claim 1, wherein each of the first internal cavity and the second internal cavity is a cylindrical cavity.

8. The surgical hammer of claim 1, wherein the first internal cavity and the second internal cavity have an overall volume of about 40% to 70% of an overall volume of the hammer head.

9. The surgical hammer of claim 1, wherein the bore is positioned about a proximal end of the hammer head.

10. The surgical hammer of claim 1, wherein the bore is positioned about the longitudinal midportion of the hammer head.

11. The surgical hammer of claim 1, wherein the slot is an elongated slot having a longitudinal axis parallel to a longitudinal axis of the shaft.

12. The surgical hammer of claim 1, wherein the hammer includes a convex surface defining the proximal end of the slot.

13. The surgical hammer of claim 1, wherein the hammer head has a substantially cylindrical overall profile.

14. The surgical hammer of claim 1, wherein the hammer head has an overall weight of about 100 grams to 5 kilograms.

15. The surgical hammer of claim 1, wherein the bore is a blind bore.

16. A surgical hammer comprising:
    a handle;
    a shaft extending from the handle; and
    a substantially cylindrical hammer head connected to the shaft about a proximal end and a longitudinal midportion of the hammer head, the hammer head including:
       an elongated tapered slot extending through the hammer head and in fluid communication with a distal end of the hammer head,
       a bore extending into the hammer head sized to receive the shaft,
       a cylindrical first internal cavity within the hammer head spaced laterally from the elongated tapered slot and at least partially filled with metal ball bearings or shot, and
       a cylindrical second internal cavity within the hammer head spaced laterally from the elongated tapered slot and at least partially filled with metal ball bearings or shot, wherein the elongated tapered slot is distal to the bore at the longitudinal midportion of the hammer head, between the cylindrical first internal cavity and the cylindrical second internal cavity.

17. The surgical hammer of claim 16, wherein the first internal cavity and the second internal cavity have an overall volume of about 40% to 70% of an overall volume of the hammer head.

18. The surgical hammer of claim 16, wherein the hammer head has an overall weight of about 100 grams to 5 kilograms.

19. The surgical hammer of claim 16, wherein the metal ball bearings or shot occupy, by volume, from about 20% to about 95% of a total internal volume of the first internal cavity and the second internal cavity.

20. The surgical hammer of claim 16, wherein the bore is a blind bore.

* * * * *